United States Patent
Hwang et al.

(10) Patent No.: US 8,046,056 B2
(45) Date of Patent: Oct. 25, 2011

(54) BODY FAT MEASUREMENT APPARATUS AND METHOD OF OPERATING THE APPARATUS

(75) Inventors: In Duk Hwang, Suwon-si (KR); Kun Soo Shin, Seongnam-si (KR); Beop Min Kim, Wonju-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 684 days.

(21) Appl. No.: 11/892,459

(22) Filed: Aug. 23, 2007

(65) Prior Publication Data

US 2008/0058617 A1    Mar. 6, 2008

(30) Foreign Application Priority Data

Aug. 31, 2006  (KR) ................ 10-2006-0083724

(51) Int. Cl.
*A61B 6/00* (2006.01)
(52) U.S. Cl. ..................................... 600/476
(58) Field of Classification Search ............. 600/473, 600/476, 310
See application file for complete search history.

(56) References Cited

U.S. PATENT DOCUMENTS

| 6,285,904 B1 | 9/2001 | Weber et al. |
| 2005/0288591 A1 | 12/2005 | Kondoh et al. |

FOREIGN PATENT DOCUMENTS

| EP | 0 516 251 A2 | 3/1992 |
| JP | 08-308813 | 11/1996 |
| JP | 2003-265440 | 9/2003 |
| JP | 2004-350836 | 12/2004 |
| JP | 2005-125059 | 5/2005 |
| JP | 2005-230160 | 9/2005 |
| KR | 2001-0099267 | 11/2001 |
| KR | 10-2006-0032048 | 4/2006 |

OTHER PUBLICATIONS

European Search Report issued on Feb. 29, 2008 in corresponding European Patent Application 07114809.2.
Office Action issued in corresponding Korean Patent Application No. 10-2006-0083724; mailed on Apr. 28, 2008.

*Primary Examiner* — Michael Rozanski
(74) *Attorney, Agent, or Firm* — Staas & Halsey LLP

(57) ABSTRACT

A method measuring a body fat by using a body fat measurement device including an optical detector and at least two light sources, the method including: detecting an optical signal which is scattered by a biological tissue by the optical detector, and measuring a first optical signal intensity and a second optical signal intensity; calculating a slope the first optical signal intensity and the second optical signal intensity by using a distance between a first light source unit and a second light source unit, and a difference between the first optical signal intensity and the second optical signal intensity, the first optical signal intensity corresponding to the first light source unit and the second optical signal intensity corresponding to the second light source unit; and measuring a thickness of body fat of the biological tissue from the calculated slope.

8 Claims, 8 Drawing Sheets

BODY FAT MEASUREMENT APPARATUS AND METHOD OF OPERATING THE APPARATUS

CROSS-REFERENCE TO RELATED APPLICATION

This application claims the benefit of Korean Patent Application No. 10-2006-0083724, filed on Aug. 31, 2006, in the Korean Intellectual Property Office, the disclosure of which is incorporated herein by reference.

BACKGROUND

1. Field

The present invention relates to a body fat measurement device and method, and more particularly, to a body fat measurement device and method which can measure a thickness of body fat by using a relation between a distance of at least two light sources and an optical signal intensity which is detected from a biological tissue corresponding to each light source.

2. Description of the Related Art

Health and beauty are critical issues for people living in modern society, accordingly a wellbeing trend seeking a healthy and enjoyable life is currently booming. One criterion for health estimation is measuring an obesity rate. There are various methods of measuring the obesity rate, and a body fat ratio is usually one of criteria for measuring the obesity rate, and also the body fat ratio may be one criterion for people on a diet for beauty purposes.

The methods of measuring a body fat ratio include a body average density measurement measuring weight in the water, a skinfold test calculating the body fat ratio by measurement thickness of fat in a specific point of a body, a body impedance analysis calculating the body fat ratio by measuring a resistance in a body by flowing a weak current in the body, a weight and waist relation table measuring the body fat ratio by using a weight and a waist size, and the like. However these methods need mostly complicated equipment and are inaccurate when measuring the body fat ratio.

Currently, a body fat measurement method using a light is suggested to readily and accurately measure body fat with a simple equipment. A body fat measurement device using the light is based on a theory that when a light emitted from a light source is emitted at a measurement point of a body, backward scattering occurs in the body, and subsequently a body fat is measured by measuring a scattered optical signal using an optical detector.

In comparison to other body fat measurement methods, the above-described body fat measurement method is non-invasive, and may quickly measure the thickness of body fat. Accordingly, the body fat measurement device is manufactured in a small size and is generally included in a portable device. Here, the accuracy of measurement must be guaranteed without being restricted to a certain time, place, or operator when measuring the thickness of body fat. However, a portable body fat measurement device according to the conventional art is manufactured in a small size, and constructed as a portable device or installed in a mobile terminal and the like. Thus, the portable body fat measurement device may not accurately measure the thickness of body fat at all times.

Accordingly, a body fat measurement device which a user can carry without restriction to a certain time or a certain place, and accurately measure thickness of body fat is required.

SUMMARY

An aspect of the present invention provides a body fat measurement device and method which can more effectively measure a thickness of body fat by calculating a distance between at least two/three light source unit and an optical signal intensity that is detected from a biological tissue corresponding to each light source.

An aspect of the present invention also provides a body fat measurement device and method which can more readily and accurately measure a thickness of body fat by calculating the thickness of body fat using a relation between a slope or a ratio of slopes and the thickness of body fat. Here, the slope is calculated using a distance between at least two/three light source units and an optical signal intensity corresponding to each light source.

According to an aspect, there is provided a method of measuring a body fat by using a body fat measurement device including an optical detector and at least two light sources, the method including: detecting an optical signal which is scattered from a biological tissue by the optical detector, and measuring each optical signal intensity; calculating a slope with respect to a first optical signal intensity and a second optical signal intensity by using a distance between a first light source unit and a second light source unit of the at least two light sources, and a difference between the first optical signal intensity and the second optical signal intensity, the first optical signal intensity corresponding to the first light source unit and the second optical signal intensity corresponding to the second light source unit; and measuring a thickness of body fat of the biological tissue from the calculated slope.

According to another aspect, there is provided a method of measuring a body fat by using a body fat measurement device including an optical detector and at least light sources, the method including: detecting an optical signal which is emitted from each of the at least three light sources to a biological tissue, and measuring each optical signal intensity; calculating a first slope with respect to a first optical signal intensity and a second optical signal intensity by using a distance between a first light source unit and a second light source unit of the at least three light source units, and a difference between the first optical signal intensity and the second optical signal intensity, the first optical signal intensity corresponding to the first light source unit and the second optical signal intensity corresponding to the second light source unit; calculating a second slope with respect to a third optical signal strength and a fourth optical signal intensity by using a distance between a third light source unit and a fourth light source of the at least three light source units, and a difference between the third optical signal intensity and the fourth optical signal intensity, the third optical signal intensity corresponding to the third light source and fourth optical signal intensity corresponding to the fourth light source unit; and measuring a thickness of body fat of the biological tissue by using a ratio of the second slope to the first slope.

According to yet another aspect, there is provided a body fat measurement device including: at least two light sources emitting a light to a biological tissue; an optical detector detecting an optical signal, which is scattered from the biological tissue, and converting the detected optical signal into an electrical signal; an optical signal intensity measurement unit measuring the intensity of the detected optical signal; and a body fat measurement unit measuring a thickness of body fat of the biological tissue by using a distance between the light source unit and the optical signal intensity corresponding to each of the light source units.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF THE EMBODIMENTS

Figure 1:
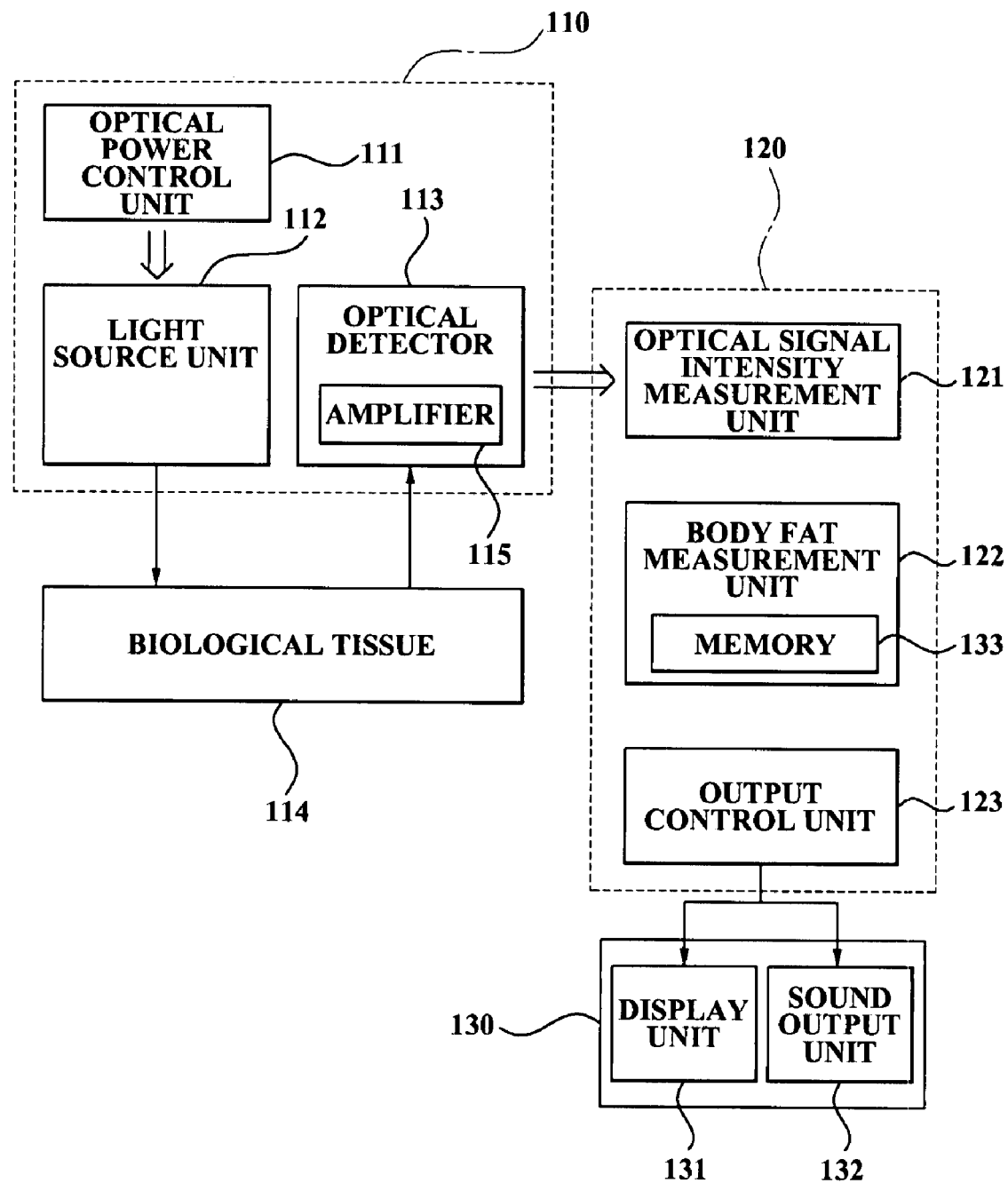
FIG. 1 is a block diagram illustrating a configuration of a body fat measurement device according to an exemplary embodiment.

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

A body fat measurement device including an optical sensor module according to the present invention may be included in any one of a mobile terminal, a personal digital assistant (PDA), a portable game device, an MP3 player, a personal multimedia player (PMP), a digital multimedia broadcasting terminal (DMB) terminal, a portable blood sugar measurement device, and a grip power exercise device. Specifically, the body fat measurement device according to the present invention may be embodied by constructing the optical sensor module included in the body fat measurement device according to the present invention as a part of the above-described portable devices. Also, the body fat measurement device may not be installed in the devices, but may be designed to have a stand-alone configuration.

Also, a biological tissue used throughout the present specification is not defined to a human body. Specifically, the body fat measurement device including the optical sensor module according to the present invention may be utilized for all living things that have a subcutaneous fat layer between the skin and muscle.

Hereinafter, exemplary embodiments of the present invention will be described in detail with reference to the accompanying drawings.

FIG. 1 is a block diagram illustrating a configuration of a body fat measurement device according to an exemplary embodiment.

The body fat measurement device according to the present invention may include an optical sensor module 110, an electrical signal calculation unit 120 and an output unit 130. The optical sensor module 110 may include an optical power control unit 111, a light source unit 112, and an optical detector 113. The electrical signal calculation unit 120 may include an optical signal intensity measurement unit 121, a body fat measurement unit 122 and an output control unit 123. The output unit 130 may include a display unit 131 and a sound output unit 132.

The light source unit 112 of the optical sensor module 110 may include at least two light sources. The light sources may be configured in a form of a point light source that includes a widely-utilized top view light emitting diode (LED). Also, the light sources may be configured into a form of a light surface source. Also, the light sources may include a side view LED in addition to the top view LED. When the top view LED is utilized for the light source, it will be described with reference to FIG. 2.

Figure 2:
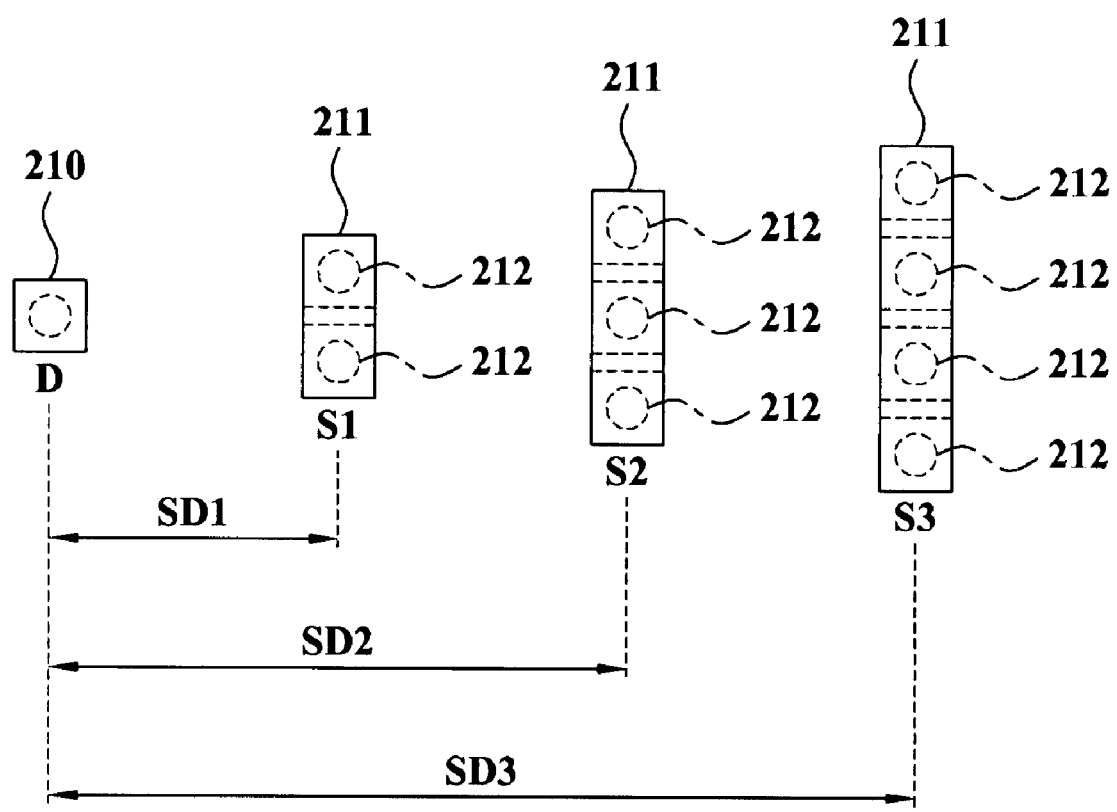
FIG. 2 is a diagram illustrating a top view of an optical sensor module in a body fat measurement device according to an exemplary embodiment.

FIG. 2 is a diagram illustrating a top view of an optical sensor module in a portable body fat measurement device according to an exemplary embodiment.

In FIG. 2, a top view of an optical detector 210 of an optical sensor module 110 and the light source unit 112 are illustrated. According to an embodiment of the present invention, at least two light source units may be established. Specifically, to measure the thickness of body fat, at least two light source units may be established. Also, at least three light source units may be installed. As a number of the light source units increase, a reference of a reflected light, which may be used for the measurement of the body fat for the measurement point, increases, therefore accuracy of a measurement result may be improved. When three light source units S1, S2, and S3 are established will be described with reference to FIG. 2.

The at least two light source units 112 and the optical detector 210 are horizontally arranged, such as illustrated in FIG. 2, and each of the light source units S1, S2, and S3 is horizontally arranged and spaced apart from the optical detector 210 by distances SD1, SD2, and SD3, respectively.

Each of the light source units S1, S2, and S3 includes a light source 212 and a guide unit 211. At least one light source 212 may be established in each of the light source units S1, S2, and S3. Specifically, as illustrated in FIG. 2, each of the light source units S1, S2, and S3 horizontally arranged with the optical detector 210 may be constructed to include at least one light source 212. A number and a location of establishment of the light source 212 may be variously embodied by those skilled in the art. As described above, the light source 212 may be configured into any one of a point light source that includes a widely-utilized top view LED, and a surface light source, both of which include an LED.

The guide unit 211 perpendicularly guides the light emitted from the light source 212 to be emitted towards a measurement point. Since a general top-view LED has a great radiation angle, intensity of a light which is outputted to a perpendicular direction tends to decrease. Thus, the guide unit 211 may minimize the decrease of the light by reducing the radiation angle of the light from the LED and guiding the light in the measurement point in a perpendicular direction. For the above operation, the guide unit 211 may be embodied as a prism sheet. Also, the guide unit 211 may include various units used in the art, in addition to the prism sheet.

As described above, the light from the light source 212 is perpendicularly emitted towards the measurement point via the guide unit 211. In this case, the light is emitted towards a top surface of the guide unit 211, i.e. the light is emitted in a type of a surface light, and the emitted light is as much as a dimension of the top surface of the guide unit 211

Each of the light source units S1, S2, and S3 including the light source 212 and guide unit 211 are spaced apart from the optical detector 210 by a predetermined distance, i.e. the light source unit S1 may be spaced apart from the optical detector 210 by a distance SD1, the light source S2 may be spaced apart from the optical detector 210 by a distance SD2, and the light source S3 may be spaced apart from the optical detector 210 by a distance SD3. The distances SD1, SD2, and SD3 between each of the light source units S1, S2, and S3 and the optical detector 210 may be variously established according to a threshold of the thickness of the body fat measurable in the measurement point. Specifically, when values of the distances SD1, SD2, and SD3 are increased, the threshold of the thickness of the body fat, measurable in the measurement point, also comparatively increases. According to an exemplary embodiment of the present invention, the distance between the light source S1 and the optical detector 210 may be set to 2 mm to 5 mm to adjust for the epidermis.

Also, optical powers outputted from the light source 212 of each of the light source units S1, S2, and S3 may be constructed to increase according to the distances from the optical detector 210. Specifically, the optical powers may increase in an order of an optical power outputted from the light source 212 of the light source unit S1, an optical power outputted from the light source 212 of the light source unit S2, and an optical power outputted from the light source 212 of the light source unit S3. In this instance, the optical powers may be controlled by the optical power control unit 111. Wavelengths of the lights from each of the light sources 212 may be set to be identical to each other.

Also, the light source unit 112 including the light source 212 and the guide unit 211 may be constructed to have a thickness of less than approximately 1.5 mm to be installed in a mobile terminal. As described above, a slimmer light source unit may be embodied by establishing at least two light sources in an array type to the guide unit 211. Accordingly, the optical sensor module 110 according to the present invention may be optimized to be installed in the mobile terminal where a thickness is extremely limited to establish components within the mobile terminal.

Also, a slimmer but comparatively greater surface light source may be embodied by arranging each top view light source in an array type in the guide units 211, regardless of thickness or a size of the mobile terminal.

Figure 3:
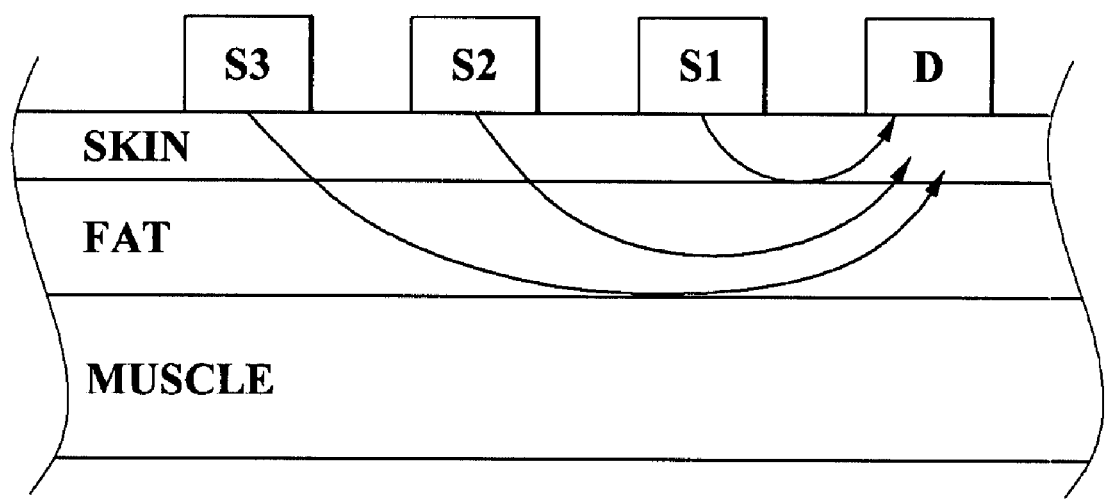
FIG. 3 is a diagram illustrating a side view of an optical sensor module in a body fat measurement device according to an exemplary embodiment.

FIG. 3 is a diagram illustrating a side view of an optical sensor module in a body fat measurement device according to an exemplary embodiment of the present invention.

As described with FIG. 2, each of light source units S1, S2, and S3 illustrated in FIG. 3 may be provided to be spaced apart from an optical detector D by a corresponding distance. The optical power control unit 111 may control the amount of an operational current which is applied to each of the light source units S1, S2, and S3 so that optical powers may increase in an order of greater distances. Specifically, the amount of the operational current applied to the light source unit S3 may be greater than the amount of the operational current applied to the light source unit S2. Also, the amount of the operational current applied to the light source unit S2 may be greater than the amount of the operational current applied to the light source unit S1.

Referring again to FIG. 1, the optical power control unit 111 controls operational current which is applied to the at least one light source of the light source unit 112. Specifically, when the light source unit 112 includes a plurality of light sources, the optical power control unit 111 may control the operational current which is applied to each of the light sources so that the optical power outputted from each of the light sources may increase in proportion to the distance between the optical detector 113 and each light source.

The optical detector 113 receives a scattered light which is emitted to an inside of a biological tissue 114, and transforms the received scattered light into an electrical signal. Specifically, the optical detector 113 receives the scattered light, which is scattered from a measurement point, i.e. from the biological tissue 114, and transforms the scattered light into an electrical signal. Here, the optical detector 113 may include an optical-electrical transducing element which transforms an optical signal into an electrical signal.

The optical signal intensity measurement unit 121 measures the intensity of the optical signal which is detected by the optical detector 113. The optical signal intensity measurement unit 121 may measure the optical signal intensity by correcting an optical power outputted from each light source and a predetermined amplifier gain. Specifically, as described above, the optical signal intensity measurement unit 121 may measure the optical signal intensity after standardizing the optical signal intensity by considering the optical power, which changes based on the distance between the light source and the optical detector 113, and the predetermined amplifier gain, which is acquired by amplifying the detected optical signal from the optical detector 113 using a amplifier 115.

Specifically, when an optical power emitted from each of the light source units S1, S2, and S3 is different, and an amplifier gain amplifying an optical signal, detected from each of the light source units S1, S2, and S3, is different, the optical signal intensity measurement unit 121 may perform the standardization to correct the difference in the size of the optical power outputted from each light source unit and the amplifier gain using the same condition.

For example, referring to FIG. 3, when it is assumed that the optical power of the light source unit S1 is 1, the optical power of the light source unit S2 is 2, and the optical power of the light source unit S3 is 3, the optical signal intensity measurement unit 121 may correct an optical signal intensity, measured from the light source unit S2 by the light detector 113, to ½, and may correct an optical signal intensity, measured from the light source unit S3 by the light detector 113, to ⅓. Specifically, the optical signal intensity measurement unit 121 may perform the standardization of each optical signal intensity to assume that the same optical signal intensity is emitted from each of the light source units S1, S2, and S3.

Also, the optical signal intensity measurement unit 121 may perform the standardization based on an amplifier gain amplifying each optical signal. For example, when an amplifier gain amplifying an optical signal detected from the light source unit S1 is 1, another amplifier gain amplifying an optical signal detected from the light source unit S2 is 2, and still another amplifier gain amplifying an optical signal detected from the light source unit S3 is 3, the optical signal intensity measurement unit 121 may correct the intensity of the optical signal detected from the light source unit S2, to ½, and correct the intensity of the optical signal detected from the light source unit S3, to ⅓. Specifically, the optical signal intensity measurement unit 121 may perform the standardization of each optical signal intensity to assume that the same amplifier gain amplifies an optical signal detected from each of the light source units S1, S2, and S3.

The body fat measurement unit 122 measures the thickness of body fat of the biological tissue 114 by using the distance between light sources and the detected optical signal intensity corresponding to each of the light sources.

According to an embodiment, a body fat measurement method of the body fat measurement unit 122 may be classified into two embodiments. According to a first exemplary embodiment, the thickness of body fat may be measured by calculating at least one slope from at least two optical signals, and using the slope and a predetermined function. According to a second exemplary embodiment, the thickness of body fat may be measured by calculating at least two slopes from at least three optical signals, and using a ratio between the slopes and a predetermined function.

The body fat measurement unit 122 maintains the function according to the first exemplary embodiment and the function according to the second exemplary embodiment, to measure the thickness of body fat. Here, the function may be implemented by a program in a form of an algorithm that is selected from a predetermined experiment. Thus, the body fat measurement unit 122 may include a memory 133 where the program including the function algorithm is recorded. The function may be experimentally acquired from a relation between the thickness of body fat and a slope between optical signal strengths, which will be described in detail later.

According to the first exemplary embodiment of the present invention, the body fat measurement unit 122 calculates a slope with respect to a first optical signal intensity and a second optical signal intensity by using a distance between a first light source unit and a second light source unit of at least two light source units, and a difference between the first optical signal intensity and the second optical signal intensity. Here, the first optical signal intensity corresponds to the first light source unit and the second optical signal intensity corresponds to the second light source unit, which will be described with reference to FIG. 4.

Figure 4:
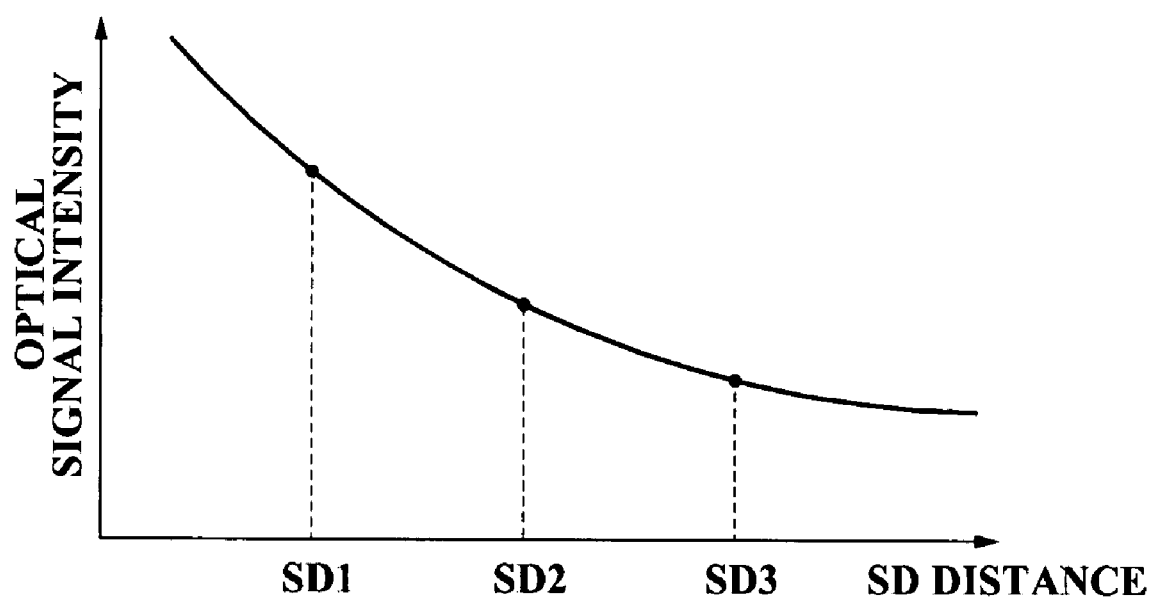
FIG. 4 is a graph showing a relation between a distance from an optical detector to each light source, and an optical signal intensity, which is measured by a body fat measurement device according to an exemplary embodiment.

FIG. 4 is a graph showing a relation between a distance from an optical detector to each light source unit, and an optical signal intensity, which is measured by a body fat measurement device according to an exemplary embodiment.

As shown in FIG. 4, when light is emitted to a biological tissue using a first light source unit, a second light source unit, and a third light source unit, and an optical signal corresponding to each light source unit is detected from the biological tissue using an optical detector, the optical signal intensity is in inverse proportion to the distance between the optical detector and the light source unit. In the graph, distance SD1 designates the distance between the first light source unit and the optical detector, distance SD2 designates the distance between the second light source unit and the optical detector, and distance SD3 designates the distance between a third light source unit and the optical detector. The body fat measurement unit 122 may calculate the slope with respect to the first light source unit and the second light source unit.

Specifically, the body fat measurement unit 122 may calculate the slope by using the difference between the optical signal intensity corresponding to the first light source, i.e. the optical signal intensity corresponding the distance SD1, and the optical signal intensity corresponding to the second light source, i.e. the optical signal intensity corresponding to the distance SD2, and the distance between the first light source unit and the second light source unit, i.e. SD2-SD1. Here, the body fat measurement unit 122 may calculate the slope by taking a log value for each of the optical signal intensities.

Referring again to FIG. 1, the body fat measurement unit 122 calculates the slope, and then measures the thickness of body fat by using the slope and the function of the first exemplary embodiment. The function according to the first exemplary embodiment will be described with reference to FIG. 5.

Figure 5:
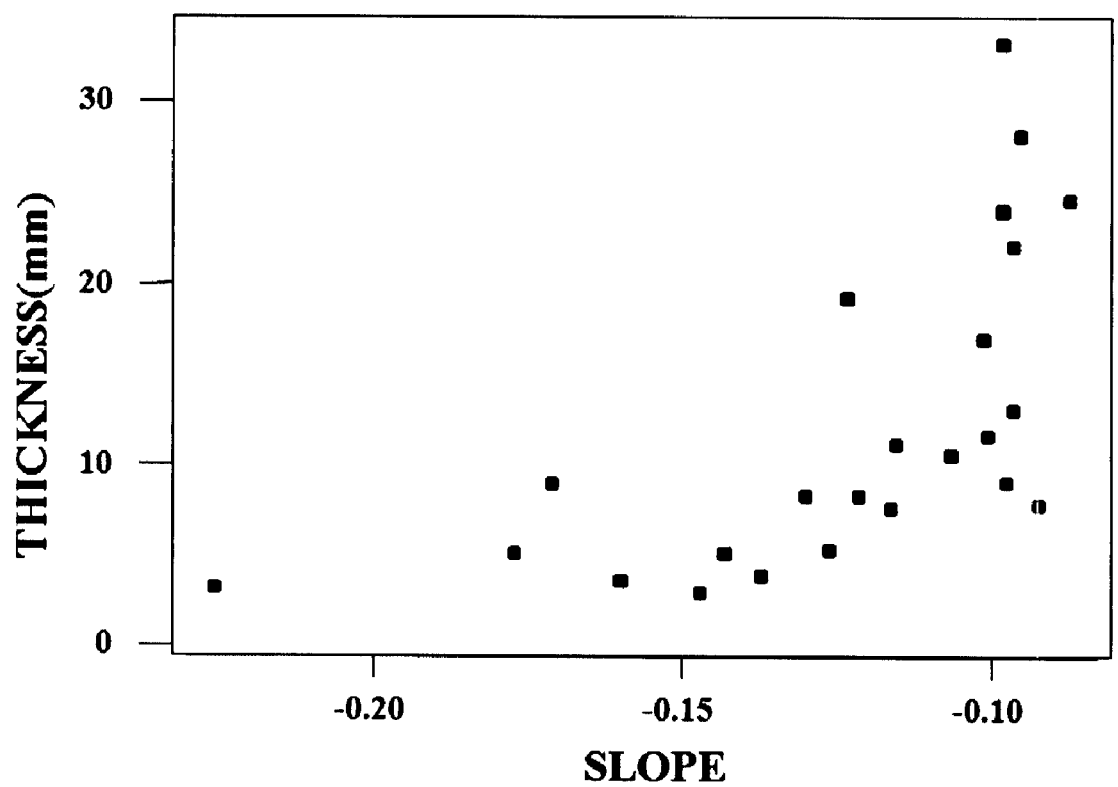
FIG. 5 is a graph showing a relation between a slope and a thickness of body fat according to a first exemplary embodiment.

FIG. 5 is a graph showing a relation between a slope and a thickness of body fat according to the first exemplary embodiment.

The graph of FIG. 5 shows results of measuring the thickness of body fat with respect to a biological tissue, and calculating a slope according to a distance between two light sources, from the biological tissue, using a body fat measurement device according to the first exemplary embodiment. Specifically, the thickness of body fat corresponds to the result of measurement using a computed tomography (CT) scan, and the slope corresponds to the result of measurement using the body fat measurement device according to the first exemplary embodiment. The measurements were performed with respect to a plurality of users and various abdominal portions of each user.

In the graph, each data indicated by 24 points designates results which are obtained by measuring the thickness of body fat with respect to four abdominal portions for every six users, that is, a total of 24 abdominal portions, using a CT scan, and measuring optical signal intensity and a slope between a light source and an optical detector with respect to 24 abdominal portions using the body fat measurement device. Specifically, the thickness of body fat (vertical axis) corresponding to each data was measured using the CT scan, and the slope (horizontal axis) was measured using the body fat measurement device. As described above, the slope may be calculated by dividing the difference between the optical signal intensity detected from the first light source and the optical signal intensity detected from the second light source by the distance between the first light source and the second light source.

As shown in FIG. 5, the thickness of body fat is in proportion to the slope. Specifically, as the slope increase, the thickness of body fat also increases. Thus, a body fat thickness measurement function using the slope as a parameter may be acquired from the relation between the slope and the thickness of body fat.

A relation between the slope and the thickness of body fat may be obtained by calculating a regression equation with respect to a dispersion of each data indicated by points in the graph of FIG. 5. The regression equation calculation with respect to the dispersion may be performed through various types of regression equation calculation programs that are widely used in the art.

As a result of calculating the regression equation with respect to the dispersion of the data, the regression equation with respect to the data shown in the graph of FIG. 5 was "y=31.8+157x". Here, y indicates the thickness of body fat, measured using the CT scan, corresponding to the vertical axis of the graph, and x indicates the slope ratio, measured using the body fat measurement device, corresponding to the horizontal axis.

Also, as a result of calculating a pearson correlation between the slope ratio and the thickness of body fat with respect to the 24 data, a value of 0.604 was obtained. Accordingly, as known from the regression equation and the pearson correlation, the thickness of body fat and the slope have a linear proportion relation therebetween.

Therefore, according to the first exemplary embodiment, the body fat thickness measurement function may be set to "thickness of body fat=second constant+(first constant*slope)". In the present exemplary embodiment, the first constant may be set to 157 and the second constant to 31.8. Also, the first constant and the second constant may be set to various values within a predetermined error range, depending upon experiment results of those skilled in the art.

Accordingly, the body fat measurement unit 122 may calculate the thickness of body fat by using the body fat thickness measurement function and the calculated slope. As described above, according to the first exemplary embodiment, the body fat may be more effectively and accurately measured by using the slope, which is calculated based on the optical signal intensity and the distance between light source units, for the body fat measurement function and thereby measuring the thickness of body fat.

According to the second exemplary embodiment, the body fat measurement unit 122 calculates a first slope with respect to a first optical signal intensity and a second optical signal intensity by using a distance between a first light source unit and a second light source units of at least three light source units, and a difference between the first optical signal intensity and the second optical signal intensity. Here, the first optical signal intensity corresponds to the first light source unit and the second optical signal intensity corresponds to the second light source unit. Also, the body fat measurement unit 122 calculates a second slope with respect to a third optical signal intensity and a fourth optical signal intensity by using a distance between a third light source unit and a fourth light source unit of the at least three light source units, and a difference between the third optical signal intensity and the fourth optical signal intensity. Here, the third optical signal intensity corresponds to the third light source unit and fourth optical signal intensity corresponds to the fourth light source unit, respectively.

As described above via the first exemplary embodiment with reference to FIG. 4, the body fat measurement unit 122 according to the second exemplary embodiment calculates the slope using the first light source unit and the second light source unit. Also, the body fat measurement unit 122 further calculates the slope with respect to the third light source unit and the fourth light source unit. The third light source may be the first light source unit or the second light source unit. Specifically, the body fat measurement unit 122 may calculate the slope the first light source unit and the fourth light source unit, and may also calculate the slope with respect to the second light source unit and the third light source unit. The above-described descriptions may be applicable when there are three light sources.

The body fat measurement unit 122 measures the thickness of body fat by using the first slope and the second slope, and the function according to the second exemplary embodiment. The function according to the second exemplary embodiment will be described with reference to FIG. 6.

Figure 6:
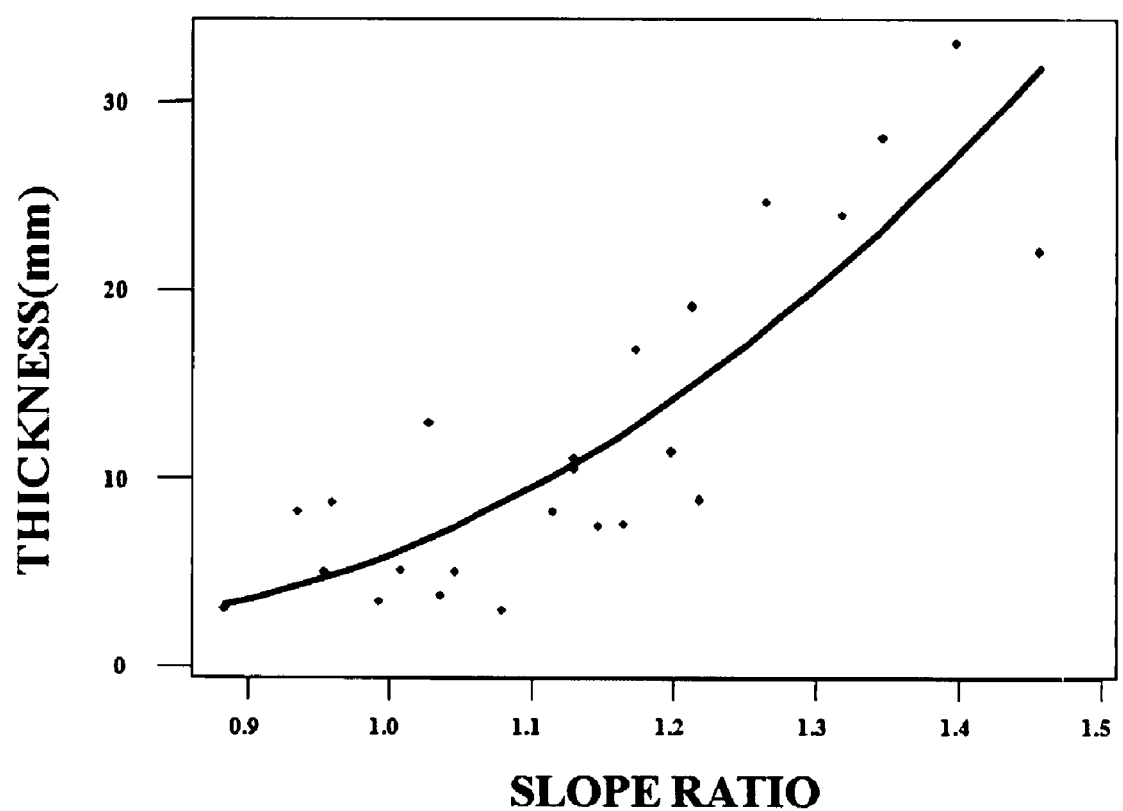
FIG. 6 is a graph showing a relation between a slope and a thickness of body fat according to a second exemplary embodiment.

FIG. 6 is a graph showing a relation between a slope and a thickness of body fat according to the second exemplary embodiment.

In FIG. 5 according to the first exemplary embodiment, the graph of FIG. 6 shows the ratio between slopes by measuring the thickness of body fat with respect to a biological tissue, calculating at least one slope according to a distance between two light sources, from the biological tissue, a body fat measurement device according to the second exemplary embodiment. Specifically, the thickness of body fat corresponds to the result of measurement a CT scan, and the slope corresponds to the result of measurement via the body fat measurement device according to the second exemplary embodiment. A slope ratio may be calculated using at least two slopes. Specifically, the slope ratio with respect to two slopes may be calculated. The slope ratio with respect to at least three slopes may be calculated.

As shown in FIG. 6, the thickness of body fat has about a quadratic proportion relation with the slope ratio. Specifically, as the slope ratio increases, the thickness of body fat also increases in quadratic proportion. Thus, a body fat thickness measurement function using the slope ratio as a parameter may be acquired from the relation between the slope ratio and the thickness of body fat.

As described above in the first exemplary embodiment of FIG. 5, a relation between the slope ratio and the thickness of body fat may be obtained by calculating a regression equation with respect to a dispersion of each data indicated by points in the graph of FIG. 6.

As a result of calculating the regression equation with respect to the dispersion of the data, the regression equation with respect to the data shown in the graph of the FIG. 6 was "$y=34.2544-86.2168x+58.0241x^2$". Here, y indicates the thickness of body fat, measured using the CT scan, corresponding to the vertical axis of the graph, and x indicates the slope ratio, measured using the body fat measurement device, corresponding to the horizontal axis of the graph.

Also, as a result of calculating a pearson correlation between the slope ratio and the thickness of body fat with respect to the data, a value of 0.839 was obtained. Accordingly, as known from the regression equation and the pearson correlation, the thickness of body fat and the slope have a linear proportion relation therebetween.

Therefore, according to the second exemplary embodiment, the body fat thickness measurement function may be set to "thickness of body fat=third constant−(first constant*slope ratio)+(second constant*slope ratio$^2$)". In the present exemplary embodiment, the first constant may be set to 86.2186, the second constant to 58.0241, and the third constant to 34.2544. Also, the first constant, the second constant, and the third constant may be set to various values within a predetermined error range, depending upon experimental results of those skilled in the art.

Accordingly, the body fat measurement unit 122 may calculate the thickness of body fat by using the body fat thickness measurement function and the calculated slope ratio. As described above, according to the second exemplary embodiment, the body fat may be more effectively and accurately measured by using the ratio between at least two slopes, which is calculated based on the optical signal intensity and the distance between light source units, for the body fat measurement function and thereby measuring the thickness of body fat.

The output control unit 123 controls information of the body fat to be displayed or played via the output unit 130. The output unit 130 may display or play the measured body fat information using the display unit 131 or the sound output unit 132.

Figure 7:
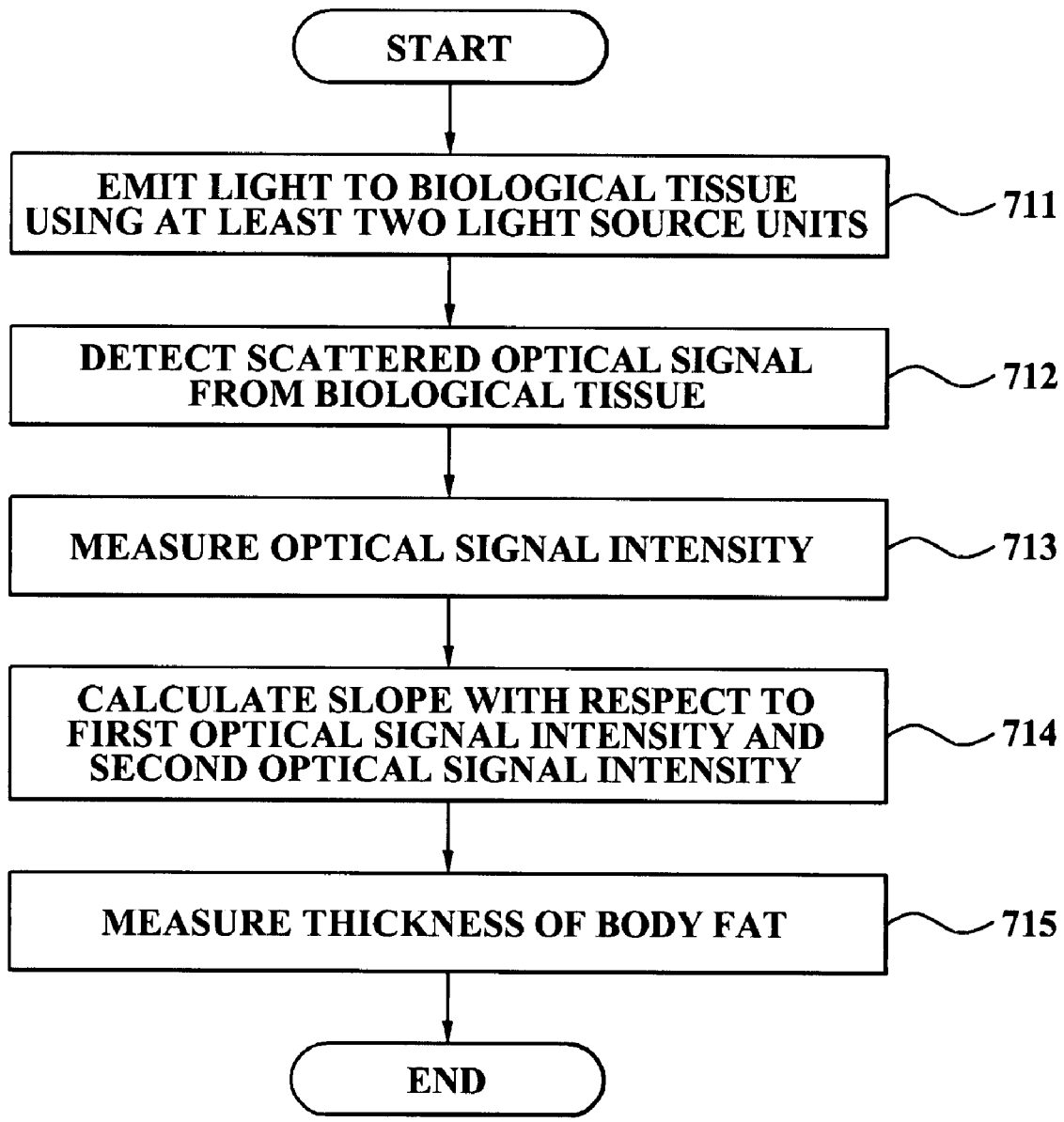
FIG. 7 is a flowchart illustrating a method of measuring a thickness of body fat according to a first exemplary embodiment.

FIG. 7 is a flowchart illustrating a method of measuring a thickness of body fat according to the first exemplary embodiment.

A body fat measurement apparatus according to the first exemplary embodiment includes an optical detector and at least two light source units. In operation 711, the body fat measurement device emits a light to a biological tissue using each of the at least two light source units. In operation 712, the body fat measurement device detects an optical signal, which is emitted from the biological tissue from each of the at least two light source units and scattered, using the optical detector.

In operation 713, the body fat measurement device measures the intensity of the detected optical signal.

In operation 714, the body fat measurement device calculates a slope with respect to a first optical signal intensity and a second optical signal intensity by using a distance between a first light source unit and a second light source unit of the at least two light sources, and a difference between the first optical signal intensity and the second optical signal intensity. The first optical signal intensity corresponds to the first light source unit and the second optical signal intensity corresponds to the second light source unit.

Also, in operation 714, the body fat measurement device may calculate the slope by calculating a log value of the first optical signal intensity and a log value of the second optical signal intensity by taking a log for the first optical signal intensity and the second optical signal intensity, and dividing a difference between the log value of the first optical signal intensity and the log value of the second optical signal intensity by the distance between the first light source and the second light source.

In operation 715, the body fat measurement device measures the thickness of body fat of the biological tissue by multiplying the slope by a first constant and adding a second constant to the result of the multiplication. Here, the first constant may be set to 157 and the second constant to 31.8.

Figure 8:
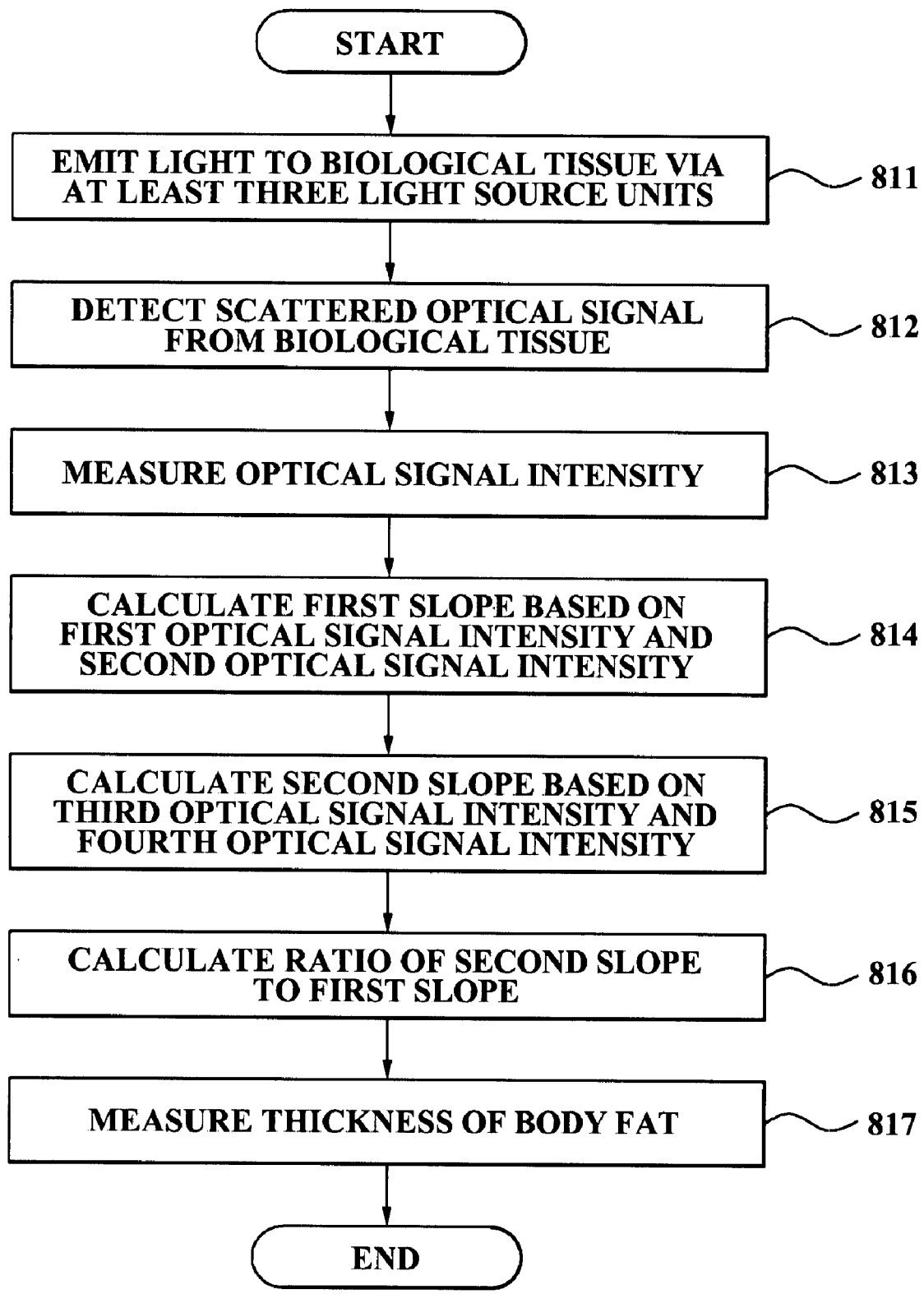
FIG. 8 is a flowchart illustrating a method of measuring a thickness of body fat according to a second exemplary embodiment.

FIG. 8 is a flowchart illustrating a method of measuring a thickness of body fat according to a second exemplary embodiment.

A body fat measurement apparatus according to the second exemplary embodiment includes an optical detector and at least three light source unit. In operation 811, the body fat measurement device emits a light to a biological tissue using each of the at least three light source units. In operation 812, the body fat measurement device detects an optical signal, which is emitted from the biological tissue from each of the at least two light sources and scattered, using the optical detector. In operation 813, the body fat measurement device measures the intensity of the detected optical signal.

In operation 814, the body fat measurement device calculates a first slope with respect to a first optical signal intensity and a second optical signal intensity by using a distance between a first light source unit and a second light source unit, and a difference between the first optical signal intensity and the second optical signal intensity. The first optical signal intensity corresponds to the first light source unit and the second optical signal intensity corresponds to the second light source unit.

Also, in operation 814, the body fat measurement device may calculate the first slope by calculating a log value of the first optical signal intensity and a log value of the second optical signal intensity by taking a log for the first optical signal intensity and the second optical signal intensity, and dividing a difference between the log value of the first optical signal intensity and the log value of the second optical signal intensity by the distance between the first light source unit and the second light source unit.

In operation 815, the body fat measurement device calculates a second slope based on a third optical signal intensity and a fourth optical signal intensity by using a distance between a third light source unit and a fourth light source unit of the at least three light sources, and a difference between the third optical signal intensity and the fourth optical signal intensity. The third optical signal intensity corresponds to the third light source unit and the fourth optical signal intensity corresponds to the fourth light source unit.

Also, in operation 815, the body fat measurement device may calculate the second slope by calculating a log value of the third optical signal intensity and a log value of the fourth optical signal intensity by taking a log for the third optical signal intensity and the fourth optical signal intensity, and dividing a difference between the log value of the third optical signal intensity and the log value of the fourth optical signal intensity by a distance between the third light source unit and the fourth light source unit.

In operation 816, the body fat measurement device calculates the ratio by dividing the first slope by the second slope.

In operation 817, the body fat measurement device measures the thickness of body fat by calculating the ratio by dividing the first slope by the second slope, calculating a first value by multiplying the ratio by a first constant, calculating a second value by multiplying the square of the ratio by a second constant, and subtracting the first value from a third constant and adding the second constant to the result of the subtraction. Here, the first constant may be set to 86.2186, the second constant to 58.0241, and the third constant to 34.2544.

Although briefly described, the body fat measurement method according to the first exemplary embodiment and the second exemplary embodiment, which has been described with FIGS. 7 and 8, may include body fat measurement operations according to the first exemplary embodiment and body fat measurement operations according to the second exemplary embodiment using the body fat measurement device of the present invention, which has been described with FIGS. 1 through 6.

The body fat measurement method according to the above-described embodiment of the present invention may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, and the like, including a carrier wave transmitting signals specifying the program instructions, data structures, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

According to the above-described exemplary embodiments of the present invention, a body fat measurement device and method may more effectively measure a thickness of body fat by calculating a distance between at least two/three light sources and an optical signal intensity that is detected from a biological tissue corresponding to each light source.

Also, according to the above-described exemplary embodiments of the present invention, a body fat measurement device and method may more readily and accurately measure a thickness of body fat by calculating the thickness of body fat using a relation between a slope or a ratio of slopes and the thickness of body fat. Here, the slope is calculated using a distance between at least two/three light sources and an optical signal intensity corresponding to each light source.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A method of measuring a body fat by using a body fat measurement apparatus comprising an optical detector and at least two light source units, the method comprising:

illuminating a biological tissue with a first light source unit with a corresponding first source intensity and a second light source unit with a second source intensity;

detecting an optical signal which is scattered from the biological tissue, and measuring an optical signal intensity corresponding to the at least two light source units;

calculating a slope based on a first optical signal intensity and a second optical signal intensity by using a distance between the first light source unit and the second light source unit of the at least two light source units, and a difference between the first optical signal intensity and the second optical signal intensity, the first optical signal intensity corresponding to the first light source unit and the second optical signal intensity corresponding to the second light source unit, respectively; and measuring a thickness of body fat of the biological tissue from the calculated slope, wherein the first optical source intensity and the second optical source intensity are different from each other due to using different numbers of light sources.

2. The method of claim 1, wherein the measuring the optical signal intensity comprises:

standardizing each of the optical signal intensities by correcting an optical power outputted from each light source unit and an amplifier gain.

3. The method of claim 1, wherein the calculating comprises:

calculating a log value of the first optical signal intensity and a log value of the second optical signal intensity by taking a log for the first optical signal intensity and the second optical signal intensity; and dividing a difference between the log value of the first optical signal intensity and the log value of the second optical signal intensity by the distance between the first light source unit and the second light source unit.

4. The method of claim 1, wherein the measuring the thickness of body fat further comprises:

multiplying the slope by a first constant and adding a second constant to the result of the multiplication.

5. The method of claim 4, wherein the first constant is 157 and the second constant is 31.8.

6. The method of claim 1, wherein the second optical source intensity is about 2 times of the first optical source intensity.

7. A non-transitory computer-readable recording medium storing an executable program for implementing a method of measuring a body fat by using a body fat measurement device comprising an optical detector and at least two light source units, the method comprising:

illuminating a biological tissue with a first light source unit with a corresponding first source intensity and a second light source unit with a second source intensity;

detecting an optical signal which is scattered from the biological tissue by the optical detector, and measuring an optical signal intensity corresponding to the at least two light source units;

calculating a slope with respect to a first optical signal intensity and a second optical signal intensity by using a distance between the first light source unit and the second light source unit of the at least two light source units, and a difference between the first optical signal intensity and the second optical signal intensity, the first optical signal intensity corresponding to the first light source unit and the second optical signal intensity corresponding to the second light source unit; and measuring a thickness of body fat of the biological tissue from the calculated slope, wherein the first optical source intensity and the second optical source intensity are different from each other due to using different numbers of light sources.

8. A body fat measurement apparatus comprising:

at least two light source units, including a first light source unit with a corresponding first source intensity and a second light source unit with a corresponding second source intensity, configured to emit a light to a biological tissue;

an optical detector configured to detect an optical signal, which is scattered from the biological tissue, and to convert the detected optical signal into an electrical signal;

an optical signal intensity measurement unit configured to measure an intensity of the detected optical signal corresponding to the at least two light source units; and a body fat measurement unit configured to measure a thickness of body fat of the biological tissue by calculating a slope based on a first optical signal intensity and a second optical signal intensity by using a distance between the first light source unit and the second light source unit, and a difference between the first optical signal intensity and the second optical signal intensity, wherein the first optical source intensity and the second optical source intensity are different from each other due to using different numbers of light sources.

* * * * *

UNITED STATES PATENT AND TRADEMARK OFFICE
CERTIFICATE OF CORRECTION

| | |
|---|---|
| PATENT NO. | : 8,046,056 B2 |
| APPLICATION NO. | : 11/892459 |
| DATED | : October 25, 2011 |
| INVENTOR(S) | : In Duk Hwang et al. |

Page 1 of 1

It is certified that error appears in the above-identified patent and that said Letters Patent is hereby corrected as shown below:

Column 2 (Abstract), Line 6-7, after "slope" insert -- of --.

Signed and Sealed this
Fourteenth Day of February, 2012

David J. Kappos
*Director of the United States Patent and Trademark Office*